United States Patent [19]

Bansemir et al.

[11] Patent Number: 4,900,721

[45] Date of Patent: Feb. 13, 1990

[54] DISINFECTANTS AND THEIR USE FOR DISINFECTING THE SKIN AND MUCOUS MEMBRANE

[75] Inventors: Klaus Bansemir, Langenfeld; Karlheinz Disch, Haan; Klaus Hachmann, Hilden; Rudolf Lehmann, Leichlingen; Manfred Biermann, Muelheim; Harald Schnegelberger, Leichlingen, all of Fed. Rep. of Germany

[73] Assignee: Henkel Kommanditgesellschaft auf Aktien, Duesseldorf, Fed. Rep. of Germany

[21] Appl. No.: 60,138

[22] Filed: Jun. 9, 1987

[30] Foreign Application Priority Data

Jun. 9, 1986 [DE] Fed. Rep. of Germany ....... 3619376
Feb. 2, 1987 [DE] Fed. Rep. of Germany ....... 3702983

[51] Int. Cl.$^4$ .................. A61K 7/48; A01N 31/02; A01L 2/16; C11D 3/48
[52] U.S. Cl. ........................... 514/25; 424/49; 424/55; 514/23; 514/714; 514/901
[58] Field of Search ............... 424/49, 55; 514/901, 514/23, 25, 714

[56] References Cited

U.S. PATENT DOCUMENTS

| | | | |
|---|---|---|---|
| 1,563,346 | 12/1925 | Downs | 514/714 |
| 2,684,924 | 7/1954 | Rose et al. | 167/30 |
| 2,990,425 | 6/1961 | Senior | 260/501 |
| 3,468,898 | 9/1969 | Cutler et al. | 260/301 |
| 3,535,422 | 10/1970 | Cox et al. | 514/714 |
| 3,547,828 | 12/1970 | Mansfield et al. | 252/351 |
| 3,598,865 | 8/1971 | Lew | 260/210 |
| 3,707,535 | 12/1972 | Lew | 260/210 |
| 3,772,269 | 11/1973 | Lew | 260/210 |
| 3,839,318 | 10/1974 | Mansfield | 260/210 |
| 3,843,779 | 10/1974 | Norfleet | 424/54 |
| 4,022,834 | 5/1977 | Gundersen | 260/564 |
| 4,053,636 | 10/1977 | Eustis, III et al. | 424/326 |
| 4,129,517 | 12/1978 | Eggensperger et al. | 514/714 |
| 4,198,392 | 4/1980 | Juneja | 424/48 |
| 4,302,441 | 11/1981 | Muhlemann et al. | 514/714 |
| 4,349,669 | 9/1982 | Klahr et al. | 536/127 |
| 4,420,484 | 12/1983 | Gorman et al. | 424/326 |
| 4,518,585 | 5/1985 | Greene et al. | 514/714 |
| 4,537,778 | 8/1985 | Clipper et al. | 424/49 |
| 4,627,972 | 12/1986 | Gioffre et al. | 424/49 |
| 4,748,158 | 5/1988 | Biermann et al. | 514/635 |
| 4,804,530 | 2/1989 | Sampathkumar | 424/49 |

FOREIGN PATENT DOCUMENTS

| | | |
|---|---|---|
| 77167 | 4/1983 | European Pat. Off. |
| 2437844 | 6/1974 | Fed. Rep. of Germany |
| 2904217 | 8/1980 | Fed. Rep. of Germany |
| 702268 | 1/1954 | United Kingdom |
| 1152243 | 5/1969 | United Kingdom |

*Primary Examiner*—Ronald W. Griffin
*Attorney, Agent, or Firm*—Ernest G. Szoke; Wayne C. Jaeschke; Real J. Grandmaison

[57] ABSTRACT

Liquid, aqueous disinfectants based on alcohol and hydrogen peroxide which contain one or more $C_2$–$C_8$ alcohols, hydrogen peroxide or a compound which forms peroxide in aqueous phase, one or more carboxylic acids, one or more microbicidally active nitrogen-containing organic compounds, one or more microbicidally active phenolic compounds, and optionally other active substances and/or auxiliaries typically present in disinfectants, and to the use of such disinfectants for disinfection of the skin and mucous membrane.

31 Claims, No Drawings

DISINFECTANTS AND THEIR USE FOR DISINFECTING THE SKIN AND MUCOUS MEMBRANE

BACKGROUND OF THE INVENTION

1. Field of the Invention

This invention relates to improved disinfectants based on a prototype formulation of alcohols and hydrogen peroxide and to the use of these disinfectants for disinfecting the skin and mucous membrane.

2. Description of Related Art

Water-based skin disinfectants containing alcohols in addition to hydrogen peroxide are known from the prior art. They combine the known antimicrobial effect of alcohols with the oxidizing effect of hydrogen peroxide and have the advantage of being free from iodine or resorbable iodine compounds which are unwanted in many areas of disinfection. Disinfectants of this type are described, for example, in German published application No. 29 04 217. The disinfectants described there are primarily intended to be used for disinfecting hands in the medical field, particularly before putting on surgical gloves, and are particularly advantageous because they are free from germ spores and are capable of killing off germ spores which have penetrated the skin. However, these disinfectants have an alcohol content of at least 50% by weight. Alcohol contents as high as these are undesirable in disinfectants formulated for disinfecting mucous membrane because they have a very strong irritant effect on the mucous membrane. Another disadvantage lies in the fact that the alcohol content of such disinfectants "vanishes" after a relatively short time in view of the relatively high vapor pressure of the alcohol so that the disinfecting effect diminishes or disappears altogether.

It has been found that disinfectants based on alcohol, for example ethanol, n-propanol and/or i-propanol, and hydrogen peroxide, but with alcohol concentrations distinctly below 50% by weight, may also be used in principle for disinfection of the skin and also for disinfection of mucous membranes. However, the microorganism reduction sought by application of the disinfectant is only achieved after contact times of at least 2 to 3 minutes. Contact times as long as these must be regarded as unrealistic and, at least in practice, are hardly ever achieved. Accordingly, the desired success of disinfection is not achieved with disinfectants containing less than 50% alcohol.

Disinfection measures on sensitive parts of the skin and mucous membrane, as required for example before surgical operations, still present considerable problems. This is due on the one hand to the fact that such areas of skin are highly sensitive to chemical irritation and react to treatment with the known, effective and fast-acting compounds (alcohols, aldehydes, chlorine donors) with a feeling of discomfort to the onset of pain. On the other hand, treatment with compounds of this type might also be ruled out by the fact that these compounds could damage or allergize the treated tissue or by the fact that toxic side effects through resorption of the active substances are not out of the question. For example, iodine is resorbed particularly effectively through the mucous membrane. Hence, the disinfecting treatment of mucous membrane with iodine containing disinfectants or antiseptics would seriously affect the organism because of such high resorbability.

STATEMENT OF THE INVENTION

Other than in the operating examples, or where otherwise indicated, all numbers expressing quantities of ingredients or reaction conditions used herein are to be understood as modified in all instances by the term "about".

An object of the present invention is to provide an improved aqueous disinfectant based on alcohols and hydrogen peroxide which has a total alcohol content of less than 50% by weight. The invention also seeks to ensure that, in the short contact times typical of skin and mucous membrane disinfection, the treated areas of skin can be disinfected and the microorganism population on the mucous membrane, for example, reduced to such an extent that the risk of infection in surgical operations is minimized. In addition, the invention seeks to use antimicrobially active compounds which are not only extremely "friendly" to the organism and, hence, do not produce any feeling of discomfort or pain, but also complement one another rather than adversely affecting one another in their antimicrobial effect.

It has now surprisingly been found that the objects stated above are achieved by aqueous disinfectants which are formulated on the basis of alcohols and hydrogen peroxide and which, in addition, contain other compounds which are themselves antimicrobially active and that these additives are even capable of synergistically enhancing the germicidal activity of these disinfectants to such an extent that adequate bacterial reduction is guaranteed, even in the short contact times which are used in practice.

The present invention relates to liquid, aqueous disinfectants based on alcohol and hydrogen peroxide which contain one or more $C_2$–$C_8$ alcohols, hydrogen peroxide or a compound which forms peroxide in aqueous phase, one or more carboxylic acids, one or more microbicidally active nitrogen-containing organic compounds, one or more microbicidally active phenolic compounds, optionally other active substances and/or auxiliaries typically present in disinfectants, and water.

The invention also relates to the use of these disinfectants for disinfection of the skin and mucous membrane.

The liquid aqueous disinfectants of the invention contain one or more $C_2$–$C_8$ alcohols as one of their microbicidally active constituents. In one preferred embodiment of the invention, alcohols such as these are present in the disinfectant in a quantity of from 8 to 25% by weight and preferably in a quantity of from 10 to 20% by weight of active substance, based on the total weight of the disinfectant.

The compounds preferably used as the alcohol component include ethanol, n-propanol and i-propanol. According to the invention, these alcohols can be used individually or in combinations of two or all three. The individual alcohols can be present in the combinations in virtually any quantitative ratios to one another. To prepare the disinfectant, the alcohols are used either as such or in the form of mixtures with water. In another embodiment of the invention, the alcohol component is formed from a combination of benzylalcohol with one or more of ethanol, n-propanol, and i-propanol.

The disinfectants of the invention contain hydrogen peroxide or a compound which forms peroxide in aqueous phase as a further active component. "Compounds which form peroxide in aqueous phase" are understood to be components of the type which release peroxide when incorporated in the disinfectants of the invention.

Hydrogen peroxide is preferably added to the disinfectants of the invention in the form of commercial, more or less concentrated aqueous solutions. According to the invention, the concentration of peroxide or peroxide-forming compound as defined above is from 0.2 to 0.7% by weight and preferably from 0.3 to 0.6% by weight of active substance, based on the total weight of the disinfectant. In another embodiment, peracetic acid or comparable compounds can also be used in addition to or instead of hydrogen peroxide. However, it is particularly preferred to incorporate hydrogen peroxide in aqueous solution in the disinfectants of the invention.

The disinfectants of the invention contain one or more carboxylic acids as another essential active component. These carboxylic acids are present in the disinfectants in concentrations of from 0.1 to 0.5% and preferably in concentrations of from 0.2 to 0.4% by weight of active substance, based on the total weight of the disinfectant. The carboxylic acids used can be one or more of formic acid, acetic acid, propionic acid, fumaric acid, lactic acid, tartaric acid, 9-undecylenic acid, sorbic acid and benzoic acid. Although these acids can all be used either individually or in combination with one another as the carboxylic acid component of the disinfectant, it is preferred to use lactic acid in the quantities mentioned above as the carboxylic acid.

Another essential active component of the disinfectants of the invention is a microbicidally active, nitrogen-containing organic compound, of which one or more can be incorporated in the liquid aqueous disinfectants of the invention. According to the invention, the nitrogen-containing organic compounds are preferably present in quantities of from 0.05 to 1.0% by weight and more preferably in quantities of from 0.1 to 0.5% by weight of active substance, based on the total weight of the disinfectant.

The nitrogen-containing organic compounds used can be any of the compounds which show adequate microbicidal activity in disinfectants in the above concentrations. Another requirement which the nitrogen-containing organic compounds suitable for the purposes of the invention have to satisfy is that they lend themselves readily to incorporation in the liquid, aqueous disinfectants without their incorporation leading to phase separation or to interactions in the sense of a reduction in microbicidal activity in the presence of the other constituents of the disinfectant.

In other preferred embodiments of the invention, the disinfectants contain one or more microbicidally active biguanide compounds as the nitrogen-containing organic compound. These microbicidally active biguanide compounds can be selected from oligohexamethylene biguanides corresponding to the following general formula

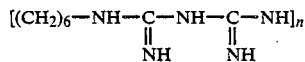 (I)

in which n is a number of at least 2 and preferably from 4 to 6, and microbicidally active bis-biguanides, and also water-soluble, non-toxic addition salts of the above two classes of compounds.

The oligomeric biguanides corresponding to general formula (I) above and their water-soluble, non-toxic salts, which can be used in accordance with the invention as biguanide compounds, and also their production, are described in GB Nos. 702,268 and 1,152,243 and in German published application No. 24 37 844. Examples of biguanide salts which are particularly suitable for use in the disinfectants according to the invention, are the corresponding water-soluble mineral acid salts, more especially the hydrochlorides. It is particularly preferred to use the oligohexamethylene biguanide hydrochloride commercially available as "Vantocil TM IB" from ICI.

Other compounds which can be present as nitrogen-containing, organic microbicidally active compounds in other preferred embodiments of the disinfectants of the invention are cocosalkyl propylenediamine guanidinium diacetate, N,N'-(1,10-decanediyl-di-1-[4H]-pyridinyl-4-ylidene)-bis-(1-octane-amine)-dihydrochloride and $N^3$-cocosalkyl guanidinium hydrochloride. Another suitable nitrogen-containing organic compound is 5-amino-1,3-bis-(2-ethyl-hexyl)-5-methyl-hexahydropyrimidine. When used in the present disinfectants, these compounds, which can also be classified as "microbicidally active, nitrogen-containing organic compounds", lead to good to very good microbicidal activity in synergism with the other essential components of the disinfectants. The disinfectants containing one or more of the above-mentioned compounds produce particularly good results in disinfection of the skin and mucous membrane.

The combination according to the invention can also contain a compound from the known class of bis-biguanides as microbicidally active, nitrogen-containing organic compounds. Bis-biguanides such as these have often been described in the relevant patent literature, cf. in particular EP No. 0 024 031; U.S. Pat. Nos. 2,684,924; 2,990,425; 3,468,898; 4,022,834; 4,053,636; German published application Nos. 22 12 259 and 26 27 548. The following are examples of compounds that can be employed herein: 1,2-bis-($N^5$-p-chlorophenyl-$N^1$-biguanido)-ethane, 1,2-bis-($N^5$-p-nitrophenyl-$N^1$-biguanido)-ethane, 1,2-bis-($N^5$-p-hydroxyphenyl-$N^1$-biguanido)ethane, 1,2-bis-($N^5$-p-chlorobenzyl-$N^1$-biguanido)-ethane, 1,2-bis-($N^5$-p-bromophenyl-$N^5$-p-hexyl-$N^1$-biguanido)-ethane, 1,2-bis-($N^5$-p-chlorophenyl-$N^5$-2-ethylphenyl-$N^1$-biguanido)-ethane, 1,2-bis-($N^5$-p-chlorophenyl-$N^1$-ethyl-$N^1$-biguanido)-ethane, 1,2-bis-($N^5$-p-methoxyphenyl-$N^1$-biguanido)-ethane, 1,2-bis-($N^5$-p-methylphenyl-$N^1$-biguanido)-ethane, 1,2-bis-($N^5$-3,5-dimethylphenyl-$N^1$-biguanido)-ethane, 1,2-bis-($N^5$-2,6-dichlorophenyl-$N^1$-biguanido)-ethane 1,2-bis-($N^5$-2,6-dimethylpheyl-$N^1$-biguanido)-ethane, 1,4-bis-($N^5$-p-chlorophenyl)-$N^1$-biguanido)-butane, bis-($N^5$-p-chlorophenyl-$N^1$-biguanido)-methane and 1,3-bis-($N^5$-p-chlorophenyl-$N^1$-biguanido)-propane.

In another preferred embodiment of the invention, water-soluble salts of the above-disclosed bis-biguanides are added as microbicidally active, nitrogen-containing organic compounds to the disinfectants according to the invention. These salts are normally salts of those acids which lead to non-toxic, addition salts. Within the group of these compounds, which comprise in particular the water-soluble, non-toxic addition salts of inorganic mineral acids and lower, i.e. up to $C_6$, carboxylic acids, the hydrochlorides, acetates and gluconates of the above mentioned bis biguanides are particularly preferred.

The organic nitrogen component advantageously added to the disinfectants according to the invention is 1,1'-hexamethylene-bis-[5-(4-chlorophenyl)-biguanide] or cocosalkyl propylenediamine guanidine, of which the salts, i.e. preferably the hydrochlorides, acetates or gluconates, show particularly high microbicidal activity and which can be incorporated particularly effectively in the disinfectants of the invention. The first of the above-mentioned compounds is commercially available as the gluconate salt under the trade name "Chlorhexidine ®" and, in the interests of simplicity, is also used in that form. In addition to the compound just mentioned, the oligohexamethylene biguanide hydrochloride commercially available as "Vantocil TM IB" is a particularly preferred, microbicidally active biguanide compound in the preferred embodiments of the disinfectants of the invention. In addition, the 5-amino-1,3-bis-(2-ethylhexyl)-5-methylhexahydro-pyrimidine, commercially available as "Hexetidine ®)", can also be used with advantage as a nitrogen-containing organic compound.

The disinfectants can also contain one or more quaternary ammonium compounds in a quantity of from 0.05 to 0.1% by weight as microbicidally active, nitrogen-containing organic compounds. The microbicidal activity of quaternary ammonium compounds such as these, which may be used either individually or in admixture in addition to one or more of the other nitrogen-containing organic compounds disclosed above, is known from the prior art. According to the invention, preferred quaternary ammonium compounds are N-alkyl-N,N-dimethylbenzylammonium chloride containing long chain $C_{12}$-$C_{18}$ fatty alkyl radicals and/or n-decyloctyldimethyl-ammonium chloride and/or di-n-octyldimethylammonium chloride and/or di-n-decylmethyl alkoxyammonium propionate containing from 1 to 6 carbon atoms in the alkoxy radical and/or di-n-decyldimethylammonium chloride. A synergistic microbicidal effect can be obtained with one or more of the above-disclosed quaternary ammonium compounds in conjunction with the other essential components of the disinfectants.

The disinfectants according to the invention contain small quantities of antimicrobial phenolic compounds as another essential component. It is possible to add a single, antimicrobially active phenolic compound, although it can also be of advantage to add several antimicrobial phenolic compounds in combination with one another and hence to obtain special advantageous effects. These effects are, on the one hand, that any gaps present in the action spectrum, for example against the individual gram-negative bacteria and fungi, can be filled. On the other hand, it was surprisingly found in the formulation of the disinfectants according to the invention that an antimicrobial phenolic compound or a combination of several such compounds is capable of producing a synergistic increase in the effect of the other antimicrobial components. Accordingly, it is particularly preferred to add a combination of several antimicrobial phenolic compounds to the disinfectants according to the invention.

In one preferred embodiment, the antimicrobial phenolic compounds are added in a quantity of from 0.01 to 0.2% and preferably in a quantity of from 0.05 to 0.1% by weight of active substance, based on the total weight of the disinfectant.

According to the invention, suitable microbicidal phenolic compounds are, in particular, o-phenylphenol, benzylphenol, p-chloro-m-cresol, 2,3,4,6-tetrachlorophenol, 2,4-dichlorophenol, monochlorophenol, o-benzyl-p-chlorophenol, 2-cyclopentyl-4-chlorophenol, mono- or polychlorinated xylenes, resorcinol, 3-hydroxy-p-cymol (thymol), 4-propenyl-anisole (anethole), 4-allyl-2-methoxyphenol (eugenol), 3-isopropyl-2-methylphenol (carvacrol), and salicylic acid phenyl ester (salol), and providing they are toxicologically safe and soluble in water- the alkali metal salts and preferably the water soluble sodium salts of the above-disclosed phenolic compounds. Within this group, one or more compounds selected from o-phenylphenol, anethole, eugenol, thymol and salicylic acid phenyl ester and water soluble sodium salts thereof can be used with particular advantage. The above phenolic compounds may be synthesized and may thus be added to the disinfectants according to the invention in pure form either individually or in admixture with one another. However, it is known that several of the compounds mentioned can also be obtained from natural sources. Ethereal oils, which may also be obtained on an industrial scale from vegetable raw materials, generally contain many of the above-mentioned microbicidal phenolic compounds in more or less large quantities. According to the invention, it is also possible to add microbicidal phenolic compounds from the above-mentioned groups to the disinfectants according to the invention either individually or in admixture with one another, at least partly in the form of ethereal oils of natural origin.

In this way, not only is the synergistic effect described above obtained, i.e. the phenolic compounds synergistically enhance the microbicidal activity of the other essential components mentioned above, a certain taste is also imparted to the disinfectants according to the invention (a desirable secondary effect where the disinfectants are used in the mouth and pharynx for example), making them more acceptable to patients. In instances where one or more of the phenolic compounds disclosed above are added to the disinfectants of the invention in the form of natural concentrates of ethereal oils, the phenolic compounds can be added in the form of one or more of anise oil, star anise oil, basil oil, fennel oil, marjoram oil, clove oil, oregano oil, pimento oil, sage oil, thyme oil, and cinnamon oil. It is immaterial to the microbicidal effect and also to the synergistic effect of the phenolic compounds from the above-mentioned group whether they emanate from synthetic or natural sources; a good effect is obtained in either case.

As the structures of the above-disclosed phenolic compounds show and as is also generally known, their molecules contain one or more aromatic radicals, so that these compounds are relatively difficult to incorporate in aqueous disinfectants. In a preferred embodiment of the invention, therefore, one or more emulsifiers are added to the disinfectants. The emulsifiers are incorporated in a quantitative ratio of phenolic compound to emulsifier of from 2:1 to 1:2 and preferably in a quantitative ratio of 1:1. In addition to adducts of 35 moles ethylene oxide (EO) with hydrogenated castor oil (such products are commercially available as "Cremophor TM RH 410" and "Eumulgin TM HRE 40", suitable emulsifiers are also adducts of 30 and more moles EO with nonhydrogenated castor oil and lauric acid monoglycerol ester which are commercially available as "Eumulgin TM RO 40" and "Lauricidin TM ".

The disinfectants of the invention contain water as another essential component. The quantity of water present is normally gauged in such a way that it adds up to 100% by weight with the sum of the other essential components of the disinfectants of the invention. For example, water is generally present in the disinfectants of the invention in a quantity of from 72.6 to 91.6% by weight, based on the total weight of the disinfectants.

In addition to the above-disclosed components—described as essential—of the liquid, aqueous disinfectants of the invention, the disinfectants can optionally contain other active substances and/or auxiliaries which, in particularly preferred embodiments, not only produce additional effects, but are also capable of synergistically enhancing the microbicidal activity of the essential components.

In addition to the components disclosed above, the disinfectants of the invention can optionally contain one or more dyes in quantities of from 0.01 to 0.1% by weight of active dye substance, based on the total weight of the disinfectant. The object of adding dyes is to color the treated areas of mucous membrane to enable the disinfection measure to be monitored. Since the disinfectants of the invention are medicaments, only those dyes permitted under current legislation may be used as dyes. According to the invention, suitable dyes are those approved for such use by the U.S. Food and Drug Administration, and may include one or more of the following dyes: the sodium salt of 1'-hydroxy-1,2'-azonaphthalene-4,4'-disulfonic acid (Azorubin), the disodium salt of 6-hydroxy-5-(4-sulfophenylazo)-2-naphthalene sulfonic acid (Gelborange S), the tetrasodium salt of 4-sulfophenyl-azo-4-(7-sulfonaphthalene)-1-azo-(8-acetamido-1-hydroxy-3,5-naphthalene disulfonic acid) (Brilliant Schwarz BN), and the extract of Dactylopius coccus (Carmin). As already disclosed above, these dyes may be used either individually or in admixture with one another. By virtue of their very strong coloring properties, very small quantities of these dyes or mixtures thereof at the lower limit of the above-disclosed range, i.e. 0.005% by weight, are sufficient.

To enhance their microbicidal activity and also to increase their duration of effect, the disinfectants of the invention may also optionally contain one or more acridine compounds. The acridine compounds when present are normally present in quantities of from 0.01 to 0.2% by weight of active substance, based on the total weight of the disinfectant. It is known that acridine compounds not only have microbicidal properties, but also coloring properties and, accordingly, may also be used in the abovedescribed manner as marking agents to show where the mucous membrane has been disinfected. Accordingly, if one or more of the acridine compounds discussed hereinafter is/are used, there would no longer be any need to use a dye from the above-disclosed class of dyes permitted for medicaments.

One preferred embodiment of the invention is characterized by the use of acridine compounds of the proflavine (3,6-diaminoacridine sulfate), trypaflavine (3,6-diamino-10-methylacridinium chloride, ethacridine (2-ethoxy-6,9 diaminoacridine lactate) and acriflavine (75% 3,6-diamino-10-methylacridinium chloride+25% 3,6-diamino-acridine monohydrochloride) type.

In another preferred embodiment of the invention, one or more complexing agents for metal ions can be additionally added to the disinfectants. This is because it is known that, under suitable conditions, certain microorganisms build up additional protection through the formation of mucous-containing shells. This situation would always appear to exist in the case of microorganisms on the mucous membranes. Natural mucins contain stabilizing calcium and magnesium ions. Complexing of these metal ions by a complexing agent surprisingly resulted in destabilization of the mucous shell. Suitable calcium- and magnesium- complexing substances are complexing agents soluble in water in the medium used. They are optionally added to the disinfectants of the invention in quantities of from 0.01 to 0.5% by weight. Preferred complexing agents for the above purpose are ethylenediamine tetra-acetic acid (EDTA), nitrilotriacetic acid (NTA), hydroxyethanediphosphonic acid (HEDP) and a number of other carboxylic acids and phosphonic acids which form complexes with calcium and magnesium, providing they are soluble in water and are pharmacologically safe.

According to the invention, it may be desirable to add to the disinfectants additional substances which regulate their rheology to a certain value. These rheology regulators may be present in quantities of from 1 to 10% by weight and preferably in quantities of from 3 to 6% by weight, based on the total weight of the disinfectant. In another preferred embodiment, one or more substances from the group polyvinylpyrrolidone, methyl cellulose, hydroxyethyl cellulose, hydroxypropyl cellulose and water-soluble polyacrylates are added as rheology regulators, polyvinylpyrrolidone being particularly preferred. For example, polyvinylpyrrolidone having a K-value of from 88 to 96 and a water content of 5% by weight, of the type commercially available as "Luviskol TM" from BASF, may be added to regulate rheology. This provides for better application of the disinfectants of the invention to the skin and mucous membrane.

In addition, it is possible and particularly preferred in accordance with the invention additionally to add one or more alkyl and/or alkenyl glycosides containing from 8 to 16 carbon atoms and preferably from 10 to 14 carbon atoms in the alkyl or alkenyl radical to the disinfectants. The alkyl groups, which may be linear or branched, thus include the alkyl radicals octyl, nonyl, decyl, undecyl, dodecyl, tridecyl, tetradecyl, pentadecyl and hexadecyl. The alkenyl radicals are the unsaturated homologs of the alkyl radicals disclosed above and may also be linear or branched. The alkyl and alkenyl glycosides, which may optionally be added in accordance with the invention, may be monoglycosides or polyglycosides containing from 2 to 8 and preferably 2 or 3 glycoside residues. According to the invention, the alkyl or alkenyl glycosides may be present in the disinfectants in quantities of from 0.1 to 2% by weight. They are a known class of compounds which may be obtained by conventional methods of organic synthesis, see for example U.S. Pat. Nos. 3,839,318; 3,707,535; and 3,547,828; German published application Nos. 19 05 523; 19 43 689; 20 36 472; and 30 01 064; and European published application No. 0 077 167. They are preferably produced by reaction of glucose or oligosaccharides with $C_8$–$C_{16}$ aliphatic alcohols which may be linear or branched, saturated, mono- or poly-olefinically unsaturated and may contain, for example, up to three double bonds. Preferred glycosides contain $C_8$, $C_{10}$, $C_{14}$ or $C_{16}$ alkyl and/or alkenyl radicals, more especially linear radicals. The alkyl or alkenyl radicals may be derived from a particular alcohol, for example from lauryl alcohol or oleyl alcohol, although they may also be obtained from alcohol mixtures of the type accumulating in the industrial synthesis of fatty alcohols from naturally occurring fats and oils. Insofar as the saccharide residue is concerned, both monoglycosides in which a cyclic sugar residue is attached to the fatty alcohol and oligomeric glycosides preferably containing up to 8 or more especially up to 3 glucose or maltose residues attached by glycoside bonds are suitable. The number of sugar residues is a statistical mean value on which the distribution typical of these products is based. Alkyl and alkenyl glycosides containing from 10 to 14 carbon atoms in the hydrocarbon radical derived from the alcohol and from 1 to 2 glycoside residues and, preferably, an average of 1 to 1.5 glycoside residues are particularly preferred for the purposes of the invention.

In addition to the above components, it is also feasible to add to the liquid, aqueous disinfectants of the invention other substances which have special functions to perform in special methods or forms of application. For example, flavor-enhancing or flavor-modifying substances can be added where the disinfectants are to be used in the mouth or pharynx. Such substances include, for example, peppermint oil or other ethereal oils which modify the taste and odor of the disinfectants used in manner pleasant to the patient. As described above, this function may also be performed by the microbicidal phenolic compounds, particularly when they are used in the form of ethereal oils of natural origin in the disinfectants of the invention.

Disinfectants for the skin and mucous membrane are generally adjusted to acidic pH values of from 3.5 to 7, and preferably of from 4 to 6. The pH regulators used are advantageously the organic carboxylic acids added as an essential component which additionally develop the microbicidal activity described above. At the same time, the acids mentioned above also have the advantage that they are capable of acting as natural buffers and hence of arresting drastic changes in pH.

In one particularly preferred embodiment, the disinfectants of the invention have the following composition:
12 to 15 % by weight ethanol,
0.3 to 0.6% by weight $H_2O_2$,
0.2 to 0.4% by weight lactic acid,
0.05 to 0.5% by weight chlorhexidine gluconate or a quaternary ammonium compound,
0.05 to 0.1% by weight of a mixture of 91.4% natural peppermint oil containing approx. 90% menthol, 4% salicylic acid phenyl ester, 3.5% anethole, 0.6% eugenol and 0.5% thymol,
0 to 0.1% by weight orthophenylphenol,
3 to 6% by weight PVP (K-value 88 to 96, water content 5% by weight) and
water in a quantity which makes up the above components to 100% by weight.

All of the constituents of the disinfectants of the invention are known substances. The disinfectants are prepared simply by mixing the components together. This may also be done by methods known from the prior art.

The disinfectants of the invention are present in more or less low-viscosity form. As described above, their viscosity may largely be regulated by addition of the above-disclosed rheology regulators. If a disinfectant of relatively high viscosity is to be obtained, in a preferred embodiment of the invention a thickener is added, for example PVP, in the quantities indicated above. This facilitates application in certain cases, for example in genital or urogenital disinfection.

Where a thinly liquid, aqueous disinfectant suitable for spraying is to be obtained, it is formulated without the addition of a thickener. For oral/pharyngeal application for example, compressed air or a propellent of the type typically used in the aerosol field for the production of sprays can be used for spraying the disinfectants of the invention.

According to the invention, the liquid, aqueous disinfectants are used for disinfection of the skin and mucous membrane. Despite an alcohol concentration of less than 20% by weight, they produce excellent disinfection results. In the application of the disinfectants, the areas of skin or mucous membrane to be disinfected are exposed to the action of the disinfectant.

The invention is illustrated but not limited by the following Examples.

EXAMPLES 1 to 16

Disinfectants according to the invention of different composition were prepared by mixing together the components shown in Table 1 below. The quantities in which the individual components were used are also shown in Table 1.

The "ethereal oil" set forth in Table 1 is a mixture of the following components:
91.4% natural peppermint oil containing approx. 90% menthol;
4.0% salicylic acid phenylester (Salol TM):
3.5% anethole
0.6% eugenol and
0.5% thymol.

The "emulsifier" used is the decahydrate of an adduct of 35 moles ethylene oxide (EO) with hydrogenated castor oil commercially available as "Cremophor TM RH 410".

"QUAT" in Table 1 is the quaternary ammonium compound N-alkyl-N,N-dimethylbenzylammonium chloride containing from 12 to 14 carbon atoms in the alkyl radical.

"HEDP" is the complexing agent hydroxyethane diphosphonic acid.

The composition of the disinfectants according to Examples 1 to 16 is shown in Table 1 below where the quantities of the individual components are given in % by weight. The balance of 100% by weight is water.

TABLE 1

Composition of the disinfectants of Examples 1 to 16 (quantities in % by weight)

| Component | 1 (comp) | 2 (comp) | 3 (comp) | 4 | 5 (comp) | 6 (comp) | 7 (comp) | 8 (comp) |
|---|---|---|---|---|---|---|---|---|
| Ethanol | | | 20 | 20 | 20 | 20 | | 10 |
| i-propanol | 20 | 20 | | | | | | |
| Hydrogen peroxide | 0.5 | 0.5 | 0.5 | 0.5 | 0.5 | 0.5 | 0.5 | 0.5 |
| Lactic acid | 0.2 | 0.2 | 0.2 | 0.2 | 0.2 | 0.2 | 0.2 | 0.2 |
| Chlorhexidine digluconate | | 0.1 | 0.1 | 0.1 | | 0.1 | | |
| Ethereal oil[1] | | | | 0.1 | 0.1 | | 0.1 | 0.1 |

TABLE 1-continued

Composition of the disinfectants of Examples 1 to 16 (quantities in % by weight)

| Component | | | | | | | | |
|---|---|---|---|---|---|---|---|---|
| Emulsifier[1] | | | 0.1 | 0.1 | 0.1 | 0.1 | 0.1 | |
| Ethacridine | | | | | | | | |
| Acriflavine | | | | | | | | |
| HEDP[1] | | | | | | | | |
| o-phenyl-phenol Na | | | | | | | | |
| QUAT[1] | | | | | | | | |
| PVP | | | | | | | | |
| Water | balance | balance | balance | balance | balance | balance | balance | balance |

| | Example | | | | | | | |
|---|---|---|---|---|---|---|---|---|
| Component | 9 | 10 | 11 | 12 | 13 | 14 | 15 | 16 |
| Ethanol | 10 | 10 | 10 | 10 | 10 | 10 | 15 | 15 |
| i-propanol | | | | | | | | |
| Hydrogen peroxide | 0.5 | 0.5 | 0.5 | 0.5 | 0.5 | 0.5 | 0.5 | 0.5 |
| Lactic acid | 0.2 | 0.2 | 0.2 | 0.2 | 0.2 | 0.2 | 0.2 | 0.2 |
| Chlorhexidine digluconate | | | | 0.3 | 0.3 | 0.3 | 0.1 | |
| Ethereal oil[1] | 0.1 | 0.1 | 0.1 | 0.05 | 0.05 | 0.1 | 0.05 | 0.1 |
| Emulsifier[1] | 0.1 | 0.1 | 0.1 | 0.05 | 0.05 | 0.1 | 0.05 | 0.1 |
| Ethacridine | 0.1 | | 0.1 | | | | | |
| Acriflavine | | 0.1 | 0.1 | | | | | |
| HEDP[1] | | | | | 0.1 | | | |
| o-phenyl-phenol Na | | | | | | | 0.05 | 0.05 |
| QUAT[1] | | | | | | | | 0.05 |
| PVP | | | | | | | 5.0 | |
| Water | balance | balance | balance | balance | balance | balance | balance | balance |

[1]see foregoing text

The antimicrobial activity of the disinfectants according to the invention was tested against the following test bacteria:

1. *Staphylococcus aureus* ATCC 6538
2. *Streptococcus faecalis.*

Bacteria reduction was determined by measuring the residual bacteria content per ml using the quantitative suspension test according to the guidelines for the testing and evaluation of chemical disinfection techniques of the Deutsche Gesellschaft fur Hygiene und Mikrobioligie (DGHM) described in Zdl. Bakt. Hyg. I. Abt. Orig. B 172, 538 to 539 (1981).

EXAMPLE 17 (Comparison Example)

The disinfectants of Examples 1 and 2 were microbiologically tested by the above-mentioned suspension test using the test microorganism *Staphylococcus aureus* (see above, 1.), the test procedure being adapted to the mucous membrane conditions by including mucin, the principal constituent of the mucous of living organisms, in the test suspension. The starting bacteria content of the bacteria suspension for a dilution ratio of disinfectant to bacteria/mucin mixture of 9 ml to 1 ml was $6 \times 10^6$ bacteria/ml and for a dilution ratio of disinfectant to bacteria/mucin mixture of 7.5 ml to 2.5 ml, $15 \times 10^6$ bacteria/ml. In addition, a 1% PVP-iodine solution was tested for comparison. The results are set out in Table 2 below.

TABLE 2

| | Suspension test with comparison disinfectants | | | |
|---|---|---|---|---|
| Disinfectant of Ex. no. | Ratio of disinfectant to bacteria/mucin mixture | Residual Bacteria content/ml after | | |
| | | 1 min. | 2.5 min. | 5 mins. |
| 1 | | 600 | <10 | <10 |
| 2 | 9 ml:1 ml | <10 | <10 | <10 |

TABLE 2-continued

| | Suspension test with comparison disinfectants | | | |
|---|---|---|---|---|
| Disinfectant of Ex. no. | Ratio of disinfectant to bacteria/mucin mixture | Residual Bacteria content/ml after | | |
| | | 1 min. | 2.5 min. | 5 mins. |
| 1% PVP-iodine | | 42,000 | 235 | <10 |
| 1 | | 250,000 | 350,000 | 92,000 |
| 2 | 7.5 ml:2.5 ml | 150,000 | 20,500 | 70 |
| 1% PVP-iodine | | 150,000 | 1,500 | <10 |

Result:

The test results show that a distinct improvement in effect over the sole use of disinfectants based on alcohol/hydrogen peroxide/carboxylic acid can be obtained by the use of chlorhexidine gluconate. For a dilution ratio of 9:1 (i.e. virtually undiluted), the effect of 1% PVP iodine solutions typically used is exceeded; in the event of dilution to 75% of the original concentration (7.5:2.5), the effect of the typically used PVP iodine solutions is virtually reached.

EXAMPLE 18

The disinfectant of Example 4 according to the invention was tested against the comparison compositions of Examples 2 and 3. The contact times of the disinfectants were considerably shortened by comparison with Example 17 to create more difficult conditions corresponding to those encountered in practice.

The reduction in bacteria count $GR_t$ for a certain contact time (in the present case 15, 30, 45 and 60 seconds) is shown in Table 3 below for the individual compositions by comparison with water of standardized hardness (WSH). The reduction in bacteria count is calculated in accordance with the following formula:

$$GR_l = \log CFU (WSH) - \log CFU (D)$$

where
CFU(WSH) is the number of colony-forming units after the action of water of standardized hardness and
CFU(D) is the number of colony-forming units after the action of the disinfectant (D).

TABLE 3

Suspension test of disinfectants of Examples 2 to 4

| Example | Test bacteria* | Reduction factors after | | | |
|---|---|---|---|---|---|
| | | 15 secs. | 30 secs. | 45 secs. | 1 min. |
| 2 | Sta. aureus | >4.7 | >4.7 | >4.7 | >4.7 |
| 3 | Sta. aureus | 0.5 | 1.4 | 2.4 | 2.9 |
| 4 | Sta. aureus | >4.7 | >4.7 | >4.7 | >4.7 |
| 2 | Strep. faecalis | >4.1 | >4.1 | >4.1 | >4.1 |
| 3 | Strep. faecalis | 3.9 | 3.9 | 4.1 | 4.1 |
| 4 | Strep. faecalis | >4.1 | >4.1 | >4.1 | >4.1 |

*Starting bacteria counts: Sta. aureus = 44 × 10$^7$/ml
Strep. faecalis = 19 × 10$^7$/ml Result:
The microbiological test showed that a synergistic effect can be obtained and the effect of the other consitutents of the disinfectant considerably enhanced by the addition in accordance with the invention of a suitable etheral oil (compare Example 4 with Example 3).

EXAMPLE 19

The synergistic enhancement of effect obtained by an addition of microbicidal phenolic compounds is also demonstrated by the following test series in which the disinfectant of Example 3,5,6 and 7 (Comparison Examples) were compared with the disinfectant of Examples 4. 0.2% of beef albumin was additionally included in the test suspension. The results are shown in Table 4 below.

TABLE 4

Suspension test of disinfectants of Examples 3 to 7

| Example | Test bacteria | Reduction factor after | |
|---|---|---|---|
| | | 30 secs. | 1 min. |
| 7 | Staphylococcus aureus | 0.0 | 0.0 |
| 5 | Staphylococcus aureus | 0.9 | 2.5 |
| 6 | Staphylococcus aureus | 1.4 | 1.9 |
| 3 | Staphylococcus aureus | 3.1 | 4.0 |
| 4 | Staphylococcus aureus | 4.3 | 4.3 |

Result:
The suspension test showed that, in the absence of alcohol, no disinfecting effects could be obtained at all (compound of Example 7 (Comparison Example)). The clearest reduction in the bacteria count was obtained with a disinfectant according to the invention (Example 4) which, in addition to the basic constituents alcohol, hydrogen peroxide and carboxylic acid, also contained a biguanide compound and a phenolic, microbicidally active compound together with a emulsifier suitable for their incorporation in the disinfectant.

EXAMPLE 20

A further increase in microbicidal activity can be demonstrated by adding to the disinfectants according to the invention complexing agents capable of complexing mucous stabilizing metal ions (for example calcium and magnesium). In the present quantitative suspension test, 10% mucin was additionally included in the test suspension to form mucous. The results are shown in Table 5 below.

TABLE 5

Suspension test of disinfectants of Examples 12 and 13

| Example | Test bacteria | Reduction factor after | | |
|---|---|---|---|---|
| | | 30 secs. | 1 min. | 2 mins. |
| 12 | Sta. aureus with | 0.1 | 0.6 | 2.3 |
| 13 | 10% added mucin | 3.8 | 4.4 | 4.8 |

Result:
The suspension test in the presence of 10% mucin shows that the number of colony-forming units can be distinctly reduced in the presence of a complexing agent providing a suitable complexing agent is added to a disinfectant according to the invention to complex the mucous-stabilizing metal ions $Ca^{2+}$ and $Mg^{2+}$.

EXAMPLE 21

To illustrate the effectiveness of a particularly preferred variant of a mucous membrane disinfectant according to the invention against a natural mucous membrane flora, tests were carried out on the natural oral, glans penis and vaginal flora of healthy individuals. The disinfectant of Example 14 was used as the disinfectant. Microbiological testing was carried out by the quantitative suspension test on blood-agar plates. The reduction factors are shown in Table 6 below.

TABLE 6

Suspension test of the disinfectant of Example 14

| Bacteria | Load | Reduction factor after | | | | |
|---|---|---|---|---|---|---|
| | | 15 | 30 | 60 | 120 | 300 secs. |
| Nat. oral flora | none | 1.6 | 1.8 | 2.3 | 3.5 | 3.6 |
| | 0.2% | 1.3 | 1.3 | 2.0 | 2.3 | 2.3 |
| Nat. glans penis flora | none | 2.0 | 1.6 | 2.3 | 2.5 | 3.6 |
| | 0.2% albumin | 1.8 | 1.8 | 2.4 | 2.6 | 2.8 |
| Nat. vaginal flora | none | 2.1 | 2.7 | 4.2 | 5.0 | 6.4 |
| | 0.2% albumin | 1.6 | 2.8 | 3.5 | 5.2 | 6.2 |

Result:
As can be seen from Table 6, the disinfectant of Example 14 was capable of reducing the random, variously composed natural bacterial spectra of the pharyngeal and urogenital region by 99% in 1 minute.

EXAMPLE 22

The quantitative suspension test carried out with the disinfectant of Example 16 was intended to show that it is possible to use ammonium compounds as the nitrogen-containing organic compounds and orthophenylphenol to enhance their effectiveness. The results of the quantitative suspension test carried out on the test bacteria indicated with 0.2% of beef albumin incorporated in the test suspension are shown in Table 7 below.

TABLE 7

Suspension test of the disinfectant of Example 16

| Bacteria | Reduction factor after 1 minute |
|---|---|
| Staphylococcus aureus | 6.3 |
| Escherichia coli | 6.6 |
| Pseudomonas aeruginosa | 6.7 |
| Candida albicans | 5.5 |

We claim:
1. A liquid aqueous disinfectant composition comprising:

(a.) from about 8 to about 25% by weight of at least one $C_2$–$C_8$ alcohol;
(b.) from about 0.2 to about 0.7% by weight of active substance of hydrogen peroxide and/or a compound that forms peroxide in an aqueous medium;
(c.) from about 0.1 to about 0.05% by weight of at least one carboxlic acid;
(d.) from about 0.05 to about 1.0% by weight of at least one microbicidally active nitrogen-containing organic compound;
(e.) from about 0.01 to about 0.2% by weight of a microbicidally active phenolic compound, and the balance, water.

2. The disinfectant composition of claim 1 which also contains at least one of the following:
(f.) an emulsifying effective quantity of at least one emulsifier;
(g.) from about 0.01 to about 0.1% by weight of at least one dye;
(h.) from about 0.01 to about 0.2% by weight of at least one acridine compound;
(i.) from about 0.01 to about 0.5% by weight of at least one metal ion complexing agent;
(j.) from about 1 to about 10% by weight of a rheology regulator;
(k.) from about 0.1 to about 2% by weight of at least one alkyl or alkenyl glycoside containing from 8 to 16 carbon atoms in the alkyl or alkenyl group; and
(l.) from about 0.05 to about 0.1% by weight of a flavor enhancing or modifying agent.

3. The disinfectant composition of claim 1 wherein component (a.) is present in from about 10 to about 20% by weight.

4. The composition of claim 1 wherein component (a) is one or more of ethanol, n-propanol and i-propanol.

5. The composition of claim 1 wherein component (a) is a combination of benzylalcohol and one or more of ethanol and n-propanol and i-propanol.

6. The disinfectant composition of claim 1 wherein component (b) is present in from about 0.3 to about 0.6% by weight.

7. The disinfectant composition of claim 1 wherein component (b) is hydrogen peroxide and/or peracetic acid.

8. The composition of claim 1 wherein component (c) is present in from about 0.2 to about 0.4% by weight.

9. The composition of claim 1 wherein component (c) is at least one of formic acid, acetic acid, propionic acid, fumaric acid, lactic acid, tartaric acid, 9-undecylenic acid, sorbic acid, and benzoic acid.

10. The disinfectant composition of claim 1 wherein component (c) is lactic acid.

11. The disinfectant composition of claim 1 wherein component (d) is present in from about 0.1 to about 0.5% by weight.

12. The composition of claim 1 wherein component (d) is one or more of a biguanide compound or a bis-biguanide compound.

13. The composition of claim 1 wherein component (d) is a quaternary ammonium compound.

14. The disinfectant composition of claim 1 wherein component (d) is one or more of the following: an oligo-hexamethylene biguanide of the formula:

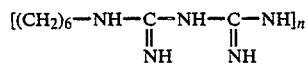

(I)

in which n is a number of at least 2, a water soluble non-toxic addition salt thereof, a bis-biguanide, a water-soluble, non-toxic addition salt thereof, 5-amino-1,3-bis-(2-ethylhexyl)-5-methyl hexahydropyrimidine, cocosalkyl propylenediamine guanidinium diacetate, N,N'-(1,10-decanediol-di-1-[4H]-pyridyl-4-ylidene)-bis-(1-octaneamine)-dihydrochloride, $N^3$-cocosalkyl guanidinium hydrochloride, and a quaternary ammonium compound.

15. The disinfectant composition of claim 1 wherein component (d) is one or more of: N-alkyl-N,N-dimethylbenzylammonium chloride, n-decyloctyl dimethylammonium chloride, di-n-octyldimethylammonium chloride, di-n-decylmethylalkoxyammonium propionate containing from 1 to 6 carbon atoms in the alkoxy radical, and di-n-decyldimethylammonium chloride.

16. The disinfectant composition of claim 1 wherein component (e) is present in from about 0.05 to about 0.1% by weight.

17. The disinfectant composition of claim 1 wherein component (e) is one or more of o-phenylphenol, p-phenylphenol, benzylphenol, p-chloro-n-cresol 2,3,4,6-tetrachlorophenol, 2,4-dichlorophenol, monochlorophenylphenol, o-benzyl-p-chlorophenol, 2-cyclopentyl-4-chlorophenol, chlorinated xylenes, resorcinol, 3-hydroxy p-cymol, 4-allyl-2-methoxyphenol, 3-isopropyl-2-methylphenol, 4-propenyl anisole, salicylic acid phenyl ester, and an alkali metal salt of any of the foregoing.

18. The disinfectant composition of claim 1 wherein component (a) is present in from about 10 to about 16%, component (b) is present in from about 0.3 to about 0.6%, component (c) is present in from about 0.2 to about 0.4%, component (d) is present in from about 0.05 to about 0.5%, and component (e) is present in from about 0.05 to about 0.1%.

19. The disinfectant composition of claim 1 wherein the composition has a pH of from about 3.5 to about 7.

20. The composition of claim 1 wherein the pH is from about 4 to about 6.

21. The disinfectant composition of claim 2 wherein component (f) is present in a quantitative ratio of component (e) to component (f) of from about 2:1 to about 1:2.

22. The disinfectant composition of claim 2 wherein component (f) is one or more of the decahydrate of an adduct of 35 moles of ethylene oxide with hydrogenated castor oil, the adduct of 30 moles of ethylene oxide with non-hydrogenated castor oil, and lauric acid monoglycerol ester.

23. The disinfectant composition of claim 2 wherein component (h) is present and is one or more of 3,6-diaminoacridine sulfate, 3,6-diamino-10-methyl acridinium chloride, 2-ethoxy-6,9-diaminoacridine lactate, and 3,6-diaminoacridine monohydrochloride.

24. The disinfectant composition of claim 2 wherein component (i) is present and is one or more of ethylenediamine tetra-acetic acid, nitrilotriacetic acid and hydroxyethane diphosphonic acid.

25. The disinfectant composition of claim 2 wherein from about 3 to about 6% of component (j) is present.

26. The composition of claim 2 wherein component (j) is present and is one or more of PVP, methylcellulose, hydroxyethylcellulose, hydroxypropylcellulose, and a water-soluble polyacrylate.

27. The disinfectant composition of claim 2 wherein component (k) is present and in which from 10 to 14 carbon atoms are present in the alkyl or alkenyl group.

28. The disinfectant composition of claim 2 wherein component (k) is present and in which from 2 to 8 glycoside residues are present.

29. The disinfectant composition of claim 28 wherein from 2 to 3 glycoside residues are present.

30. The disinfectant composition of claim 2 comprising:
   (a.) from about 12 to about 15% by weight of ethanol;
   (b.) from about 0.3 to about 0.6% by weight of $H_2O_2$;
   (c.) from about 0.2 to about 0.4% by weight of lactic acid;
   (d.) from about 0.05 to about 0.5% by weight of chlorhexidine gluconate or a quaternary ammonium compound;
   (e.) from about 0.05 to about 0.1% by weight of a mixture of 91.4% natural peppermint oil containing approx. 90% menthol, 4% salicylic acid phenylester, 3.5% anethole, 0.6% eugenol and 0.5% thymol, and from 0 to 0.1% by weight of o-phenylphenol; and
   (f.) from about 3 to about 6% by weight of PVP.

31. A method of disinfecting skin or mucous membrane comprising applying thereto a disinfectant effective quantity of the composition of claim 1.

* * * * *